US005720983A

United States Patent [19]

Malone

[11] Patent Number: 5,720,983
[45] Date of Patent: *Feb. 24, 1998

[54] TWO PACK PERACID DISINFECTION SYSTEM, METHOD OF PREPARATION OF DISINFECTANT COMPOSITION THEREFROM, AND USE THEREOF IN DISINFECTING A SURFACE

[75] Inventor: Joseph William Gerard Malone, Liverpool, United Kingdom

[73] Assignee: Solvay Interox Limited, Warrington, England

[21] Appl. No.: 481,323

[22] PCT Filed: Jan. 5, 1994

[ * ] Notice: The term of this patent shall not extend beyond the expiration date of Pat. Nos. 5,545,323 and 5,624,634.

[86] PCT No.: PCT/GB94/00010

§ 371 Date: Jul. 5, 1995

§ 102(e) Date: Jul. 5, 1995

[87] PCT Pub. No.: WO94/15465

PCT Pub. Date: Jul. 21, 1994

[30] Foreign Application Priority Data

Jan. 9, 1993 [GB] United Kingdom ............. 9300366

[51] Int. Cl.[6] ............ A01N 37/16; A01N 25/22; A01N 59/00; A61L 2/18
[52] U.S. Cl. ............ 424/616; 424/613; 424/126; 514/557; 514/558; 514/560; 514/970; 422/28; 252/186.26; 252/387; 252/389.2
[58] Field of Search ............ 514/557, 558, 514/560, 970; 424/616, 613, 126; 422/28; 252/186.26, 387, 389.2

[56] References Cited

U.S. PATENT DOCUMENTS

| 5,344,652 | 9/1994 | Hall, II et al. ............ 424/405 |
| 5,508,046 | 4/1996 | Cosentino et al. ............ 424/616 |

FOREIGN PATENT DOCUMENTS

| 0426949 | 5/1991 | European Pat. Off. |
| 9113058 | 9/1991 | WIPO |

*Primary Examiner*—John Pak
*Attorney, Agent, or Firm*—Larson & Taylor

[57] ABSTRACT

An aqueous composition comprising a lower aliphatic peracid, a corrosion inhibitor and a peroxide stabilizer and/or peracid stabilizer, is useful for disinfecting medical equipment, particularly metal components of such equipment. A process for obtaining such compositions is also provided and comprises mixing a first aqueous solution comprising a lower aliphatic peracid with a second aqueous solution comprising hydrogen peroxide, a corrosion inhibitor and a hydrogen peroxide stabilizer and/or a peracid stabilizer. The first and second aqueous solutions can form a two pack system for obtaining such compositions.

43 Claims, No Drawings

TWO PACK PERACID DISINFECTION SYSTEM, METHOD OF PREPARATION OF DISINFECTANT COMPOSITION THEREFROM, AND USE THEREOF IN DISINFECTING A SURFACE

This application is a 371 of PCT/GB94/00010, filed on Jan. 5, 1994.

This invention concerns compositions, processes for the preparation of such compositions, two-pack systems for preparing such compositions and uses of such compositions. More particularly the present invention concerns compositions comprising dilute aqueous solutions of lower aliphatic peracids and their use as disinfectant compositions.

The lower aliphatic peracids are effective wide-spectrum bactericides which have the particular advantage, in use, of leaving as residues only the corresponding lower aliphatic acids and therefore being particularly suitable for applications which require a non-environmentally-polluting disinfectant. While the lower aliphatic peracids in general are contemplated herein, for example those corresponding to carboxylic aliphatic acids containing 2 to 9 carbon atoms, peracetic acid is particularly envisaged since it is already a commercially important peracid for disinfectant purposes. Where the following description relates to peracetic acid it is to be understood that the other peracids may be read in substitution therefor provided that the technical context allows it.

Aqueous solutions of peracetic acid containing up to about 45% by weight of peracetic acid are commercially available. Such solutions may be produced by reacting appropriately concentrated hydrogen peroxide and acetic acid in an aqueous medium in the presence of an acid catalyst which is usually sulphuric acid or other strong mineral acid. The acid catalyst may be present in from about 0.1% to about 5% by weight of the reaction mixture.

Aqueous solutions of peracetic acid represent equilibrium mixtures of the reactants and the reaction products and, under relatively forcing reaction conditions, for example when using one or more of a substantial quantity of catalyst, an elevated reaction temperature and a concentrated reaction mixture, equilibrium may be substantially reached in a relatively short time. When using the strong acid catalyst in from 2% to 5% of the reaction mixture, a temperature of from 30° C. to 50° C. and a concentration of acid above about 20% by weight the reaction mixture may come to equilibrium within hours. For some applications, or where long storage is envisaged, it may not be desirable for there to be catalyst residues in a peracid product and particularly, for example, in dilute products intended for personal or domestic hygiene use. For many applications dilute solutions of peracetic acid, for example below 5% by weight but often below 2%, for example from 0.1% to 2% by weight, are required. Concentrations of peracetic acid above 0.5% by weight for example from 0.5% to 1% by weight, are particularly effective bactericidally in, for example, toilet cleansing applications. Such dilute peracetic acid solutions may be produced directly by reacting acetic acid and hydrogen peroxide in a suitably dilute reaction medium but equilibrium can take an extremely long time to reach, particularly at the more extreme dilutions envisaged. At peracid concentrations below 1% by weight, equilibrium may take a month or more to reach if the reaction is not acid catalysed or a week or more even if the reaction is acid catalysed. This entails a very heavy utilisation of plant and equipment on a large production scale.

If a concentrated equilibrium solution of peracetic acid is diluted with water, the equilibrium point of the system is progressively altered, as dilution progresses, in favour of the regeneration of the original reactants. The ageing time taken to attain the new equilibrium point, after dilution, is of a similar order to that required to produce such a dilute solution directly from suitable reactants. Such a diluted solution may be used directly, although it is not at equilibrium and is therefore of variable composition in storage. Such non-equilibrium diluted solutions also have a composition dictated by the equilibrium point applying at the original concentration, which may not be desired in some applications.

In 1955 Greenspan et al. (Proc. 42nd Ann. Mtg. Chem. Spec. Man. Ass. December 1955), disclosed that stable dilute peracetic acid solutions can be prepared by the use of peracid stabilisers in conjunction with proper adjustment of the relative concentrations of the components of the dilute peracid solution, that is to say that, if the prepared dilute solution is not fully at equilibrium, adjustment of the balance of the components can achieve stability. The solutions in question may be prepared by dilution of commercial, e.g. fully equilibrated peracetic acid which has been produced by the use of small amounts of a mineral acid catalyst.

U.S. Pat. No. 4,297,298 describes the production of an aqueous solution of a lower aliphatic peracid by preparing in a first process step a concentrated solution of the peracid from the corresponding carboxylic acid or anhydride and concentrated hydrogen peroxide in the presence of a small quantity of a strong acid catalyst and diluting the solution with a solution containing at least one of the reagents from the first process step so as to bring the concentration of the aliphatic peracid to the rated concentration of the mixture the concentration of the diluent reagent or reagents being chosen "so that once dilution has been brought about, the system is no longer at equilibrium, but tends to move in the direction of forming further aliphatic peracid at a very slow rate." The process specifically described in U.S. Pat. No. 4,297,298 produces a non-equilibrium composition which contains an extremely high concentration of hydrogen peroxide, e.g. from 28% to 46%. Such a concentration on contact with the user would cause skin bleaching and pain.

U.S. Pat. No. 4,743,447 describes the production of solutions having a hydrogen peroxide base for disinfecting contact lenses, the solution having from 0.005% to 0.1% by weight of peracetic acid, 1% to 8% by weight of hydrogen peroxide and sufficient acetic acid for the system to reach equilibrium. Such a solution may be prepared by direct reaction using a very dilute reaction mixture with lengthy equilibration or from a stable commercial solution having a "weak concentration" of peracetic acid to which the other constituents of the composition are added. This teaching does not therefore avoid the separate initial step of producing a stable weak solution of peracetic acid from which to produce in turn the final product.

EP-A-0357238 (Steris Corp) discloses an anti-microbial composition comprising a strong oxidant, a copper and brass corrosion inhibitor, a buffering agent, at least one anti-corrosive agent which exhibits corrosion inhibition in at least aluminium, carbon steel and stainless steel, and a wetting agent. The corrosion inhibitors specifically disclosed for brass and aluminium comprise triazoles and molybdates, which are known to have unfavourable toxicity, and which therefore renders undesirable their use in a medical environment.

In certain cases, it is desirable for the peracetic acid composition employed as a disinfectant composition to be produced by dilution of a more concentrated peracetic acid solution with a second solution which can comprise components which may confer beneficial properties on the peracetic acid composition, such as corrosion inhibitors. In the absence of any counter measures, or even despite them, it is possible that the second solution can become contaminated with micro-organisms, for example, moulds and yeasts, during storage prior to mixing with the peracetic acid solution. Control of this is therefore desirable, but many of the compounds commonly recommended for such control are either incompatible with peracetic acid, or can be undesirable for medical use because of their toxicity.

It is an object of the present invention to provide a disinfectant composition, based on a dilute solution of peracid, which may be used on medical equipment comprising metal components to be disinfected.

It is a further object of certain embodiments of the present invention to provide a solution suitable for diluting peracetic acid to produce a composition which may be used on medical equipment comprising metal components, such solution having improved resistance to contamination by micro-organisms.

In accordance with the present invention there is provided a process for the preparation of an aqueous disinfectant composition characterised in that the process comprises mixing a first aqueous solution comprising a lower aliphatic peracid with a second aqueous solution comprising hydrogen peroxide, a corrosion inhibitor and a hydrogen peroxide stabilizer and/or peracid stabilizer.

In another aspect, the present invention provides a disinfectant composition obtainable by a process comprising mixing a first aqueous solution comprising a lower aliphatic peracid with a second aqueous solution comprising hydrogen peroxide, a corrosion inhibitor and a hydrogen peroxide stabilizer and/or peracid stabilizer. It is to be understood that the peracid composition of the present invention is not in equilibrium and comprises a relatively higher concentration of stabilizer(s) than a skilled person would expect to find in a composition which is in equilibrium and comprises a similar concentration of peracid.

In yet another aspect, the present invention provides a two-pack system for the preparation of a disinfectant composition, characterised in that one pack comprises a first aqueous solution comprising a lower aliphatic peracid, and the other pack comprises a second aqueous solution comprising hydrogen peroxide, a corrosion inhibitor and a hydrogen peroxide stabilizer and/or peracid stabilizer.

The first aqueous solution preferably comprises a lower aliphatic peracid, such as peracetic acid, in an amount of from 2% to 10%, more preferably from 3% to 7%, by weight of the solution. The first aqueous solution may additionally comprise stabilizer(s) for the hydrogen peroxide and/or the peracid in the equilibrium solution, each relevant stabilizer being present in a preferred amount of from 20 to 10,000 ppm. Preferably both the peroxide and peracid are stabilized in the solution, giving a preferred combined stabilizer concentration of from 3000 to 6000 ppm. A suitable peracid stabilizer is dipicolinic acid and suitable peroxide stabilizers include phosphonic acids and salts thereof, e.g. the products sold by Monsanto under the trade mark "Dequest" such as hydroxyethylidenedimethylene phosphonate, diethylenetriaminepentamethylene phosphonate and ethylenediaminetetramethylene phosphonate and those stabilizers claimed in European patent application 0426949, especially cyclohexane-1,2-diaminotetramethylenephosphonic acid and salts thereof (CDTM). It should be understood that the first solution is usually an equilibrium mixture of the relevant reactants and reaction products, as generally described in the paragraph bridging page 1 and page 2 above, and that the above specified amount of peracid indicates the amount of peracid per se in the solution. A preferred process for the preparation of dilute solutions of lower aliphatic peracids useful in the present invention is disclosed in PCT Patent Application No. WO 91/13058.

The hydrogen peroxide present in the second aqueous solution is preferably present as a dilute solution. In many embodiments the concentration of hydrogen peroxide present in the second aqueous solution is unlikely to be greater than about 5% w/w. Preferably, the concentration of hydrogen peroxide is from about 0.025% w/w to about 1% w/w, most preferably from about 0.05% w/w to about 0.5% w/w and in some embodiments from 0.05% w/w to 0.2% w/w. The function of the hydrogen peroxide in the second aqueous solution is to inhibit the growth of microbial contaminants in the solution.

The second aqueous solution preferably comprises from 0.1% to 5%, more preferably from 0.1% to 1%, by weight of the solution of a corrosion inhibitor. Preferably, the corrosion inhibitor is an alkali metal phosphate, most preferably a potassium phosphate. Dipotassium hydrogen orthophosphate ($K_2HPO_4$) is the most preferred corrosion inhibitor.

The second aqueous solution preferably comprises from about 0.1% to about 2%, often 0.1% to 1%, more preferably up to 0.7% by weight of the solution of hydrogen peroxide stabilizer and/or peracid stabilizer. Preferably a hydrogen peroxide stabilizer is used. The preferred peroxide stabilizers are phosphonic acids and salts thereof, for example, those described hereinabove as suitable for the first aqueous solution. A suitable peracid stabilizer is dipicolinic acid.

In particularly preferred embodiments, the second aqueous solution comprises from 0.025% to 1% w/w hydrogen peroxide, from 0.1% to 0.7% w/w of CDTMP and from 0.1 to 1% w/w of $K_2HPO_4$.

According to certain preferred embodiments of the present invention, there is provided a two-pack system for the preparation of a disinfectant composition, characterised in that one pack comprises a first aqueous solution comprising 3% to 7% w/w peracetic acid, and the other pack comprises a second aqueous solution comprising from 0.025% to 1% w/w hydrogen peroxide, from 0.1% to 0.7% w/w CDTMP and from 0.1% to 1% w/w of dipotassium orthophosphate.

Mixing of the first and second solutions give a disinfectant composition immediately after mixing comprising at least about 0.05% and generally not greater than about 1% by weight peracid. In many embodiments, the mixture of the two solutions immediately after mixing comprises from about 0.1% to about 0.25% or from about 0.25% to about 0.5% by weight peracid. The mixture also desirably comprises from about 0.1% to about 5% corrosion inhibitor and from about 0.1% to about 1% peroxide stabilizer and/or peracid stabilizer. Such mixtures can often be obtained conveniently by selecting a volume ratio of the first solution to the second solution which is often at least 1:5 and not usually greater than about 1:50, preferably from about 1:10 to about 1:30, taking into account the concentration of the components in each solution.

One or both of the aqueous solutions may contain other components useful in disinfectant compositions, e.g. a triazole corrosion inhibitor and/or a wetting agent, though the presence of these components is not essential to obtain the advantages of the invention (indeed, such components may be slightly detrimental). One or both of the solutions may contain an indicator, such as, for example, methyl red, which undergoes a color change to indicate that the two solutions have been mixed together.

It will be appreciated that the compositions provided by the process of the present invention are not in equilibrium and that in the natural course of events the peracid component of the composition will tend towards equilibrium. For example, the composition described in the paragraph immediately above this paragraph will begin to change within a relatively short period of time from mixing the first and second solutions together and that as time passes the peracid concentration in the solution will reduce as it tends towards equilibrium. Normal equilibrium could be expected to be reached after about two days, assuming the peracid and/or peroxide does not decompose in that period.

The compositions of the present invention are particularly suitable for use as medical disinfectants. Preferably, the compositions are used to disinfect medical equipment which has metal, e.g. aluminium, brass, copper and especially steel, components required to be disinfected. For example, the composition is particularly useful for disinfection of endoscopes. The present invention may have a further advantage over the prior art compositions of Steris. The selected components of the invention composition interact to protect metal components, especially steel components, with regard to localised corrosion, eg pitting, as well as, if not better than, if molybdate, triazole and/or wetting agent were present. This is most surprising in light of the disclosure on page 4, lines 7 to 9, of Steris.

The present invention has the advantage of providing a dilute composition comprising a relatively high concentration of peracid. Furthermore, the process of the present invention enables a relatively longer shelf life for the separate aqueous solution than would be achieved if the composition was supplied per se.

The invention will now be further described, without limitation, with reference to the following examples:

EXAMPLE 1

Preparation of Composition according to the Present Invention

A solution of 5% w/w peracetic acid, 20% w/w hydrogen peroxide, 8% w/w acetic acid was diluted 14 times with a solution containing 0.1% w/w hydrogen peroxide, 1% w/w CDTMP (as supplied, 14% active w/w), 0.8% dipotassium hydrogen orthophosphate and 10 ppm 0.01% methyl red solution to form a solution containing 3,500 ppm peracetic acid.

EXAMPLE 2

Microbial Challenge Tests

A solution comprising 0.1% w/w hydrogen peroxide, 1% w/w CDTMP (as supplied, 14% active w/w) and 0.8% dipotassium hydrogen orthophosphate was tested in the German Society for Hygiene and Microbiology in vitro tests (DGHM Standards for the Examination and Determination of chemical Disinfectant Processes, 1981. In vitro tests, Determination of the bacteriostatic and fungistatic efficiency). The test organisms used were bacteria *Staphylococcus aureus*, ATCC 6538, *Pseudomonas aeruginosa*, ATCC 15442 and fungus *Candida albicans* ATCC 10231. The results of the tests showed inhibition of both bacterial and fungal growth in the solution.

A further challenge test was carried out against a solution comprising 0.4% w/w CDTMP (as 100%) and 0.8% dipotassium hydrogen orthophosphate with 0.3% w/w hydrogen peroxide. As a control the same formulation but with no hydrogen peroxide was employed. 200 ml of the solutions were challenged with 0.1 ml cultures of bacteria *Staphylococcus aureus*, ATCC 6538 (cell count $18 \times 10^8$ cfu/ml) and *Pseudomonas aeruginosa*, ATCC 15442 (cell count $3.0 \times 10^7$ cfu/ml) and fungi *Candida albicans* ATCC 10231 (cell count $1.2 \times 10^6$ cfu/ml) at the start of the test, and with *Aspergillus niger*, IMI 149007 (cell count $2.9 \times 10^7$ spores/ml) after 7 days. The samples were stored for 6 months in screw top jars at ambient temperature and regularly analysed for surviving cultures. Surviving cultures were enumerated by dilution of 1 ml samples of the solutions in quarter-strength Ringers solution followed by culture as follows. For *Staphylococcus aureus* and Pseudomonas aeruginosa, 24 hr @37° C. in Tryprone Soya Broth, for *Candida albicans*, 72 hr @37° C. in Tryprone Soya Broth, for *Aspergillus niger*, until spores develop (5–10 days) @30° C. in Malt Extract Agar. For the control solution (not according to the present invention, the number of surviving colonies was between $1.3 \times 10^6$ and $2.4 \times 10^7$ cfu/ml, with the number being $4.7 \times 10^6$ cfu/ml after 6 months. For the solution according to the present invention, there were no surviving colonies, except for 24 hours after the addition of *Aspergillus niger*, when $4 \times 10^3$ cfu/ml was observed. After a further 24 hours storage, however, there were no surviving colonies.

The results of the microbial challenge tests showed that the compositions according to the present invention gave good inhibition of microbial growth, and could give excellent resistance to microbial contamination over long term storage.

EXAMPLE 3

Chemical Stability Trials 4 samples of a solution suitable for use as a second aqueous solution in the present invention (Formulation 1) containing 0.3% w/w hydrogen peroxide, 0.14% w/w CDTMP (as 100%). 0.8% dipotassium hydrogen orthophosphate, 0.3% benzotriazole and 10 ppm 0.01% methyl red solution wore prepared. A further 4 samples containing an additional 0.2% benzotriazole (Formulation 2) were also prepared. Samples wore stored for 1 month at each of ambient (ca. 20° C.), 28° C., 32° C. and 40° C. and analysed for hydrogen peroxide content. The results of the analyses showed that for both solutions, there was no loss of hydrogen peroxide at any of the storage temperatures. The samples were also employed to produce compositions according to the present invention containing ca. 3,500 ppm peracetic acid by 14 times dilution of a solution of 5% w/w peracetic acid, 20% w/w hydrogen peroxide and 8% w/w acetic acid. The solutions according to the present invention were analysed for peracetic acid and hydrogen peroxide content, stored for 5 days and then re-analysed for peracetic acid and hydrogen peroxide. The results are given below, and show excellent chemical stability.

| Sample | 1st Day | | 5th Day | |
|---|---|---|---|---|
| Time | % $H_2O_2$ | % PAA | % $H_2O_2$ | % PAA |
| | Formulation 1 | | | |
| Initial | 2.16 | 0.37 | 2.15 | 0.24 |
| 1 month @ Temp: | | | | |
| Ambient | 2.03 | 0.37 | 2.21 | 0.26 |
| 28° C. | 2.01 | 0.34 | 2.10 | 0.24 |

-continued

| Sample Time | 1st Day %H$_2$O$_2$ | %PAA | 5th Day %H$_2$O$_2$ | %PAA |
|---|---|---|---|---|
| 32° C. | 2.05 | 0.34 | 2.11 | 0.26 |
| 40° C. | 2.04 | 0.40 | 2.10 | 0.30 |
| Formulation 2 | | | | |
| Initial | 1.98 | 0.35 | 1.99 | 0.22 |
| 1 month @ Temp: | | | | |
| Ambient | 2.06 | 0.39 | 2.08 | 0.25 |
| 28° C. | 2.08 | 0.35 | 2.11 | 0.26 |
| 32° C. | 2.12 | 0.29 | 2.11 | 0.28 |
| 40° C. | 2.06 | 0.35 | 2.02 | 0.26 |

EXAMPLE 4

Corrosivity Test

A solution of 5% w/w peracetic acid, 20% w/w hydrogen peroxide, 8% w/w acetic acid is diluted 25 times with a solution containing 0.3% w/w hydrogen peroxide, 0.14% w/w CDTMP (as 100%, <25 ppm chloride), 0.8% dipotassium hydrogen orthophosphate and 10 ppm 0.01% methyl red solution to form a disinfectant solution containing 2,000 ppm peracetic acid. Duplicate coupons of mild steel and stainless steel 316 are immersed for 72 hours in samples of the disinfectant solution at room temperature (average 20° C.). The disinfectant solution is completely replaced daily with fresh solution. Examination of the coupons on completion of the trial shows only very slight localised corrosion of the coupons.

I claim:

1. A process for the preparation of an aqueous disinfectant composition comprising mixing a first aqueous equilibrium solution comprising a lower aliphatic peracid with a second aqueous solution comprising hydrogen peroxide, a corrosion inhibitor, and a hydrogen peroxide stabilizer and/or peracid stabilizer, said hydrogen peroxide being present in said second aqueous solution in an amount of up to 5% by weight and sufficient to inhibit the growth of microbial contaminants in said second aqueous solution.

2. A two-pack system for the preparation of a disinfectant composition, one pack comprising a first aqueous equilibrium solution comprising a lower aliphatic peracid, and the other pack comprising a second aqueous solution comprising hydrogen peroxide, a corrosion inhibitor, and a hydrogen peroxide stabilizer and/or peracid stabilizer, said hydrogen peroxide being present in said second aqueous solution in an amount of up to 5% by weight and sufficient to inhibit the growth of microbial contaminants in said second aqueous solution.

3. A process as claimed in claim 1, wherein the first aqueous solution comprises a ($C_2$–$C_9$) aliphatic peracid in an amount of from 2% to 10% by weight of the solution.

4. A process as claimed in claim 3, wherein the aliphatic peracid is present in the first aqueous solution in an amount of from 3% to 7% by weight of the solution.

5. A process as claimed in claim 1 wherein the second aqueous solution comprises from 0.1% to 5% by weight of the solution of said corrosion inhibitor.

6. A process as claimed in claim 5, wherein the second aqueous solution comprises from 0.1% to 1% by weight of the solution of said corrosion inhibitor.

7. A process as claimed in claim 5 or 6, wherein the corrosion inhibitor comprises an alkali metal phosphate.

8. A process as claimed in claim 7, wherein the corrosion inhibitor comprises dipotassium hydrogen orthophosphate.

9. A process as claimed in any one of claims 1, 3, 4, 5 or 6, wherein the second aqueous solution comprises from 0.1% to about 2% by weight of the solution of said hydrogen peroxide stabilizer and/or peracid stabilizer.

10. A process as claimed in claim 9, wherein the second aqueous solution comprises from 0.1% to 0.7% by weight of the solution of said hydrogen peroxide stabilizer and/or peracid stabilizer.

11. A process as claimed in claim 1, wherein only a hydrogen peroxide stabilizer is used.

12. A process as claimed in claim 1 or claim 11, wherein the stabilizer in the second solution comprises a phosphonic acid or salt thereof.

13. A process as claimed in claim 12, wherein the stabilizer comprises cyclohexane-1,2-diaminotetramethylenephosphonic acid or salt thereof.

14. A process as claimed in claim 1, wherein the second solution comprises from about 0.025% w/w to about 1% w/w hydrogen peroxide.

15. A process as claimed in claim 1, wherein the second solution comprises from about 0.05% w/w to about 0.2% w/w hydrogen peroxide.

16. A process as claimed in claim 1, wherein the ratio of the volume of the first aqueous solution to the volume of the second aqueous solution is about 1:5 to 1:50.

17. A process as claimed in claim 1, wherein the ratio of the volume of the first aqueous solution to the volume of the second aqueous solution is about 1:10 to about 1:30.

18. A process as claimed in claim 1, wherein one or both of the first and second aqueous solutions comprises an indicator which undergoes a color change when the solutions are mixed together.

19. A process according to claim 1 or 4 wherein said aliphatic peracid comprises peracetic acid.

20. A two-pack system as claimed in claim 2, wherein the first aqueous solution comprises a ($C_2$–$C_9$) aliphatic peracid in an amount of from 2% to 10% by weight of the solution.

21. A two-pack system as claimed in claim 20, wherein the aliphatic peracid is present in the first solution in an amount of from 3% to 7% by weight of the solution.

22. A two-pack system as claimed in claim 2, wherein the second aqueous solution comprises from 0.1% to 5% by weight of the solution of said corrosion inhibitor.

23. A two-pack system as claimed in claim 22, wherein the second aqueous solution comprises from 0.1% to 1% by weight of the solution of said corrosion inhibitor.

24. A two-pack system as claimed in claim 22 or 23, wherein said corrosion inhibitor comprises an alkali metal phosphate.

25. A two-pack system as claimed in claim 24, wherein the corrosion inhibitor comprises dipotassium hydrogen orthophosphate.

26. A two-pack system as claimed in any one of claims 20, 21, 22 or 23, wherein the second aqueous solution comprises from 0.1% to about 2% by weight of the solution of said hydrogen peroxide stabilizer and/or peracid stabilizer.

27. A two-pack system as claimed in claim 26 wherein the second aqueous solution comprises from 0.1% to 0.7% by weight of the solution of said hydrogen peroxide stabilizer and/or peracid stabilizer.

28. A two-pack system as claimed in claim 2, wherein only a hydrogen peroxide stabilizer is used.

29. A two-pack system as claimed in claim 2 or claim 28, wherein the stabilizer in the second solution comprises a phosphonic acid or salt thereof.

30. A two-pack system as claimed in claim 29, wherein the stabilizer comprises cyclohexane-1,2-diaminotetramethylenephosphonic acid or salt thereof.

31. A two-pack system as claimed in claim 2, wherein the second solution comprises from about 0.025% w/w to about 1% w/w hydrogen peroxide.

32. A two-pack system as claimed in claim 2, wherein the second solution comprises from about 0.05% w/w to about 0.2% w/w hydrogen peroxide.

33. A two-pack system as claimed in claim 2, wherein the ratio of the volume of the first aqueous solution to the volume of the second aqueous solution is about 1:5 to 1:50.

34. A two-pack system as claimed in claim 2, wherein the ratio of the volume of the first aqueous solution to the volume of the second aqueous solution is about 1:10 to about 1:30.

35. A two-pack system as claimed in claim 2, wherein said one pack comprises a first aqueous solution comprising 3% to 7% w/w peracetic acid, and the other pack comprises a second aqueous solution comprising from 0.025% to 1% w/w hydrogen peroxide, from 0.1% to 0.7% w/w CDTMP and from 0.1% to 1% w/w of dipotassium orthophosphate.

36. A two-pack system as claimed in claim 2, wherein one or both of the first and second aqueous solutions comprises an indicator which undergoes a color change when the solutions are mixed together.

37. A two-pack system as claimed in claim 2 or claim 20, wherein said aliphatic peracid comprises peracetic acid.

38. In a method of disinfecting a surface which comprises contacting a surface with an aqueous disinfectant solution comprising a lower aliphatic peracid, the improvement wherein the aqueous disinfectant solution is prepared by mixing a first aqueous equilibrium solution comprising a lower aliphatic peracid with a second aqueous solution comprising hydrogen peroxide, a corrosion inhibitor, and a hydrogen peroxide stabilizer and/or peracid stabilizer, said hydrogen peroxide being present in said second aqueous solution in an amount of up to 5% by weight and sufficient to inhibit the growth of microbial contaminants in said second aqueous solution.

39. An improved method according to claim 38, wherein said first and second aqueous solutions are provided in a two-pack system, one pack comprising said first aqueous equilibrium solution and the other pack comprising said second aqueous solution.

40. An improved method according to claim 38 or 39, wherein said surface comprises metal.

41. An improved method according to claim 40, wherein said metal comprises steel.

42. An improved method according to claim 38 or 39, wherein said surface comprises a metal surface of a medical instrument.

43. A method according to claim 42, wherein said medical instrument comprises an endoscope.

* * * * *

UNITED STATES PATENT AND TRADEMARK OFFICE
CERTIFICATE OF CORRECTION

PATENT NO. : 5,720,983
DATED      : February 24, 1998
INVENTOR(S): MALONE

It is certified that error appears in the above-indentified patent and that said Letters Patent is hereby corrected as shown below:

Title page,
[*] Notice: The term of this patent shall not extend beyond the expiration date of Pat. Nos. 5,545,343 and 5,624,634.

Signed and Sealed this

Ninth Day of June, 1998

Attest:

BRUCE LEHMAN

*Attesting Officer*     *Commissioner of Patents and Trademarks*